US00PP24992P2

(12) United States Plant Patent
Heims

(10) Patent No.: US PP24,992 P2
(45) Date of Patent: Oct. 21, 2014

(54) ***BEGONIA* PLANT NAMED 'RUBY SLIPPERS'**

(50) Latin Name: *Begonia rex-cultorum*
Varietal Denomination: Ruby Slippers

(71) Applicant: Terra Nova Nurseries, Inc., Canby, OR (US)

(72) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 32 days.

(21) Appl. No.: 13/986,384

(22) Filed: Apr. 26, 2013

(51) Int. Cl.
*A01H 5/00* (2006.01)

(52) U.S. Cl.
USPC ..... Plt./343

(58) Field of Classification Search
CPC ..... A01H 5/0238
USPC ..... Plt./343
See application file for complete search history.

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Begonia* plant characterized by broad leaves colored deep ruby red with a dark star at the leaf base, maroon leaf backs, a bushy habit, light pink flowers in winter to early spring, tolerant of cool temperatures to 33° F., and excellent vigor.

1 Drawing Sheet

Botanical denomination: *Begonia rex-cultorum.*
Variety designation: 'Ruby Slippers'.

BACKGROUND

The present invention relates to a new and distinct cultivar of *Begonia*, of the family Begoniaceae, and given the cultivar name, 'Ruby Slippers'. The new cultivar originated from a cross between unknown *Begonia rex-cultorum* parents. This selection is uniquely characterized by:

1. broad leaves colored deep ruby red with a dark star at the leaf base,
2. maroon leaf backs,
3. a bushy habit,
4. light pink flowers in winter to early spring,
5. tolerant of cool temperatures to 33° F., and
6. excellent vigor.

Compared to *Begonia* 'Red Kiss' and 'Red Robin', both unpatented plants and the most similar cultivars, the new cultivar has leaves that are more red purple in color than red.

The new variety has been reproduced only by asexual propagation (leaf and stem cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers and leaf of *Begonia* 'Ruby Slippers'.

FIG. 2 shows a 1-and-a-half year old plant in a growing in a one gallon container in August in Canby. Oreg.

DETAILED PLANT DESCRIPTION

The following is a detailed description of the new *Begonia* cultivar based on observations of one-year-old specimens grown in one gallon containers in a cool greenhouse in early January in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type*.—Herbaceous rhizomatous perennial.
*Form*.—Clumping, caulescent.
*Cold hardiness*.—USDA Zone 10a.
*Size*.—Grows to 20 cm tall and 50 cm wide.
*Vigor*.—Excellent.
*Roots and rooting*.—Roots appear on leaf cuttings in 2 weeks; fine, fibrous, and white in color.

Stem:

*Type*.—Upright.
*Size*.—Grows to 7 cm long and 12 mm wide.
*Internodes*.—From 7 mm to 1 cm long.
*Lateral branches*.—None.
*Surface*.—Pubescent.
*Color*.—Brown 200C.

Leaf:

*Type*.—Simple.
*Arrangement*.—Alternate, congested.
*Number*.—About 140.
*Shape*.—Broadly ovate.
*Margins*.—Undulate, coarsely senate.
*Apex*.—Acute to acuminate.
*Base*.—Oblique.
*Venation*.—Palmate, Red Purple 187A on topside with the star pattern to Red Purple 70A where red purple, bottom side Red Purple 59A.
*Blade size*.—Grows to 17 cm wide and 19.5 cm long.
*Leaf strength*.—Excellent, tough, leathery.
*Surface texture*.—Pubescent on top and glabrous on bottom.
*Stipules*.—Deciduous, ovate-lanceolate, 23 mm long and 7 mm wide, apex acuminate and cuspidate, base clasping, entire, back side pubescent, inside glabrous, both sides Greyed Purple 183A.

*Petiole description*.—Grows to 21 cm long and 7 mm wide, succulent, pubescent, Greyed Purple 187A.

*Leaf color*.—Top side closest to Red Purple 71A with star pattern Black 202A; bottom side Purple 59A.

Inflorescence:

*Type*.—Axillary, bisexual, cymose.

*Number of flowers per cyme*.—About 4.

*Peduncle description*.—Grows 17.5 cm long and 3 mm wide, glabrous, fleshy, of good strength, Greyed Purple 183A; with 2 opposite, dehiscent petiolate leaf-bracts below each cyme, which grow to 7 mm wide and 17 mm long, margins entire and pubescent, tip apiculate, both sides glabrous, both sides Greyed Purple 183D.

*Pedicel description*.—Grow to 20 mm long, 1.5 mm wide, fleshy, of good strength, pubescent, Greyed Red 183C.

*Bloom period*.—Late fall to early winter in Canby, Oreg.

Flower bud:

*Size*.—Staminate flowers 11 mm long and 9 mm wide prior to opening; pistillate flowers are 25 mm deep and 21 mm wide prior to opening.

*Shape*.—Teardrop.

*Surface texture*.—Pubescent.

*Color*.—Red Purple 58A on tepal area, Red Purple 61C on ovary.

Flower:

*Type*.—Monoecious, bilaterally symmetrical.

*Pistillate flower*.—Grows to 23 mm deep and 38 mm wide overall; 5 fleshy tepals, reflexed, grow to 20 mm long and 18 mm wide, broadly elliptical, tip obtuse, base cuneate, margins entire, glabrous on both sides, outer tepals Purple 75A on outside and 75B on inside, inner tepals Red Purple 65D on both sides except up the middle on back side where 75B; 1 pistil, 16 mm long, ovary to 29 mm wide and 9 mm deep, three winged, two equal and one longer, Red Purple 59C to 59D, style 3 mm long and 5.5 mm wide, Yellow Orange 22A, stigma 3- branched and twisted, stigma 4 mm deep and 12 mm wide overall, Yellow Orange 22A on bottom and Yellow 8C in top.

*Staminate flower*.—10 mm deep and 27 wide, 4 tepals, glabrous on inside and pubescent on outside, 2 outer tepals 12 mm long and 11 mm wide, cupped, broadly ovate to elliptical, margin entire, tip obtuse, base obtuse, Red Purple 65B inside and 63C outside; inner tepals grow to 12 mm long and 10 mm wide, oblanceolate, entire, tip obtuse, base obtuse, both sides Red Purple 75C; stamen many in a globular head 6 mm in diameter, filament 1.5 mm long, White N155B, anthers 1 mm long and Yellow 8C, pollen none.

*Fragrance*.—None.

*Lastingness*.—A cyme blooms for about 4 weeks on the plant, flowers are self-cleaning.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

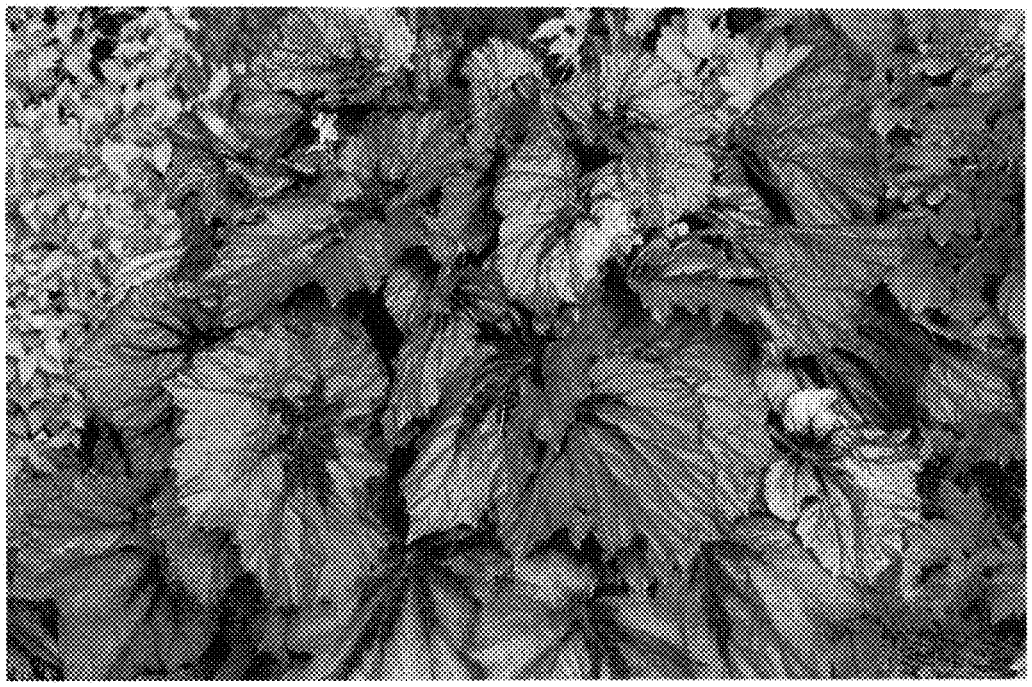

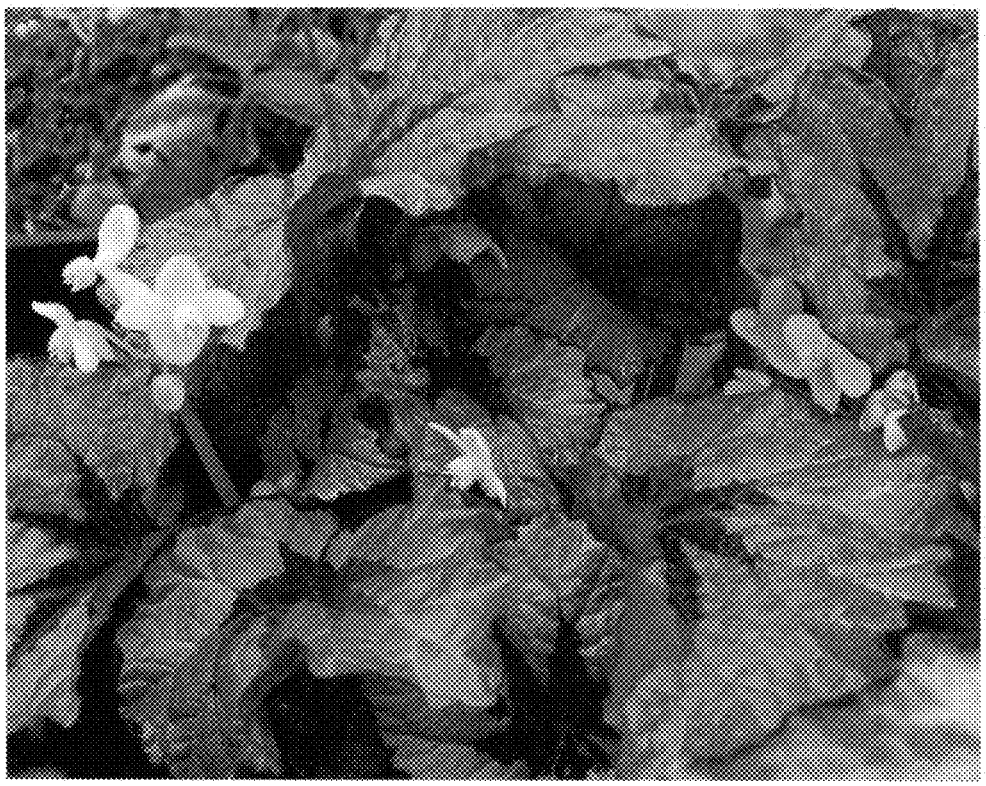
FIG. 1 above, FIG. 2 below